(12) United States Patent
Graham et al.

(10) Patent No.: US 6,814,855 B2
(45) Date of Patent: Nov. 9, 2004

(54) AUTOMATED CHEMICAL MANAGEMENT SYSTEM HAVING IMPROVED ANALYSIS UNIT

(75) Inventors: Lyndon W. Graham, Hillsboro, OR (US); Dakin Fulton, Whitefish, MT (US)

(73) Assignee: Semitool, Inc., Kalispell, MT (US)

( * ) Notice: Subject to any disclaimer, the term of this patent is extended or adjusted under 35 U.S.C. 154(b) by 329 days.

(21) Appl. No.: 09/931,283

(22) Filed: Aug. 16, 2001

(65) Prior Publication Data

US 2002/0112970 A1 Aug. 22, 2002

Related U.S. Application Data

(63) Continuation-in-part of application No. 09/387,084, filed on Aug. 31, 1999, now Pat. No. 6,356,033, which is a continuation of application No. PCT/US99/09659, filed on May 3, 1999.
(60) Provisional application No. 60/083,882, filed on May 1, 1998.

(51) Int. Cl.$^7$ ............................ G01N 27/28; G01N 27/38
(52) U.S. Cl. ................ 205/794; 205/775; 205/789; 205/81; 204/416; 204/434
(58) Field of Search ................ 205/775, 794, 205/787.5, 789, 788.5, 777.5, 775.5, 81; 204/400, 402, 403.01, 404, 405, 416, 434

(56) References Cited

U.S. PATENT DOCUMENTS

| | | |
|---|---|---|
| 3,649,509 A | 3/1972 | Morawetz et al. |
| 3,878,066 A | 4/1975 | Detike et al. |
| 3,904,493 A | 9/1975 | Losi et al. |
| 4,055,751 A | 10/1977 | Bussmann et al. |
| 4,090,926 A | 5/1978 | Matson |
| 4,132,605 A | 1/1979 | Tench et al. |
| 4,146,437 A | 3/1979 | O'Keefe |

(List continued on next page.)

FOREIGN PATENT DOCUMENTS

| | | | | |
|---|---|---|---|---|
| DE | 3118771 A1 | * | 11/1982 | .......... G01N/27/30 |
| EP | 0838541 A1 | * | 4/1998 | .......... C25D/13/24 |
| GB | 2050425 A | * | 1/1981 | .......... C25B/15/00 |
| JP | 52-017890 A | * | 2/1977 | .......... G01N/27/38 |

OTHER PUBLICATIONS

JPO abstract of JP 52–017890 A (Nishitomi et al.).*
Derwent abstract of DE 3118771 A1 (Galster).*
Z. Sun et al., *Optimized Bath Control for Void–Free Copper Deposition*, Solid State Technology, pp. 1–10, Nov. 2001.
Dennis Tench and John White, *Cyclic Pulse Voltammetric Stripping Analysis of Acid Copper Plating Baths*, Journal of the Electromechanical Society, vol. 132, No. 4, pp. 831–834, Apr. 1985.
Hobart H. Willard, et al., *Instrumental Methods of Analysis*, Fifth Edition, D. Van Nostrand Company, New York, N.Y., pp. 647–656, 1974.
Frederick A. Lowenheim, *Electroplating*, McGraw–Hill Book Company, pp. 120 & 121, 1979.

*Primary Examiner*—Alex Noguerola
(74) *Attorney, Agent, or Firm*—Edell, Shapiro & Finnan, LLC

(57) ABSTRACT

A method and apparatus for measuring a target constituent of an electroplating solution using an electroanalytical technique is set forth. In accordance with the method, at least two electrodes are employed to execute the electroanalytical technique. Gasses that are trapped or generated at the surface of one or both of the electrodes of the pair are reduced and/or removed by directing a flow of solution toward the electrode surface. This flow of solution against the electrode surface acts to automatically flush the generated gasses (typically in the form of small bubbles) from the electrode surface and generally eliminates the need for manual purging by an operator. Elimination of these gasses reduces or eliminates variability in the open circuit potential, and concomitant noise that would otherwise occur in the electroanalytical measurements.

26 Claims, 4 Drawing Sheets

U.S. PATENT DOCUMENTS

| | | | |
|---|---|---|---|
| 4,228,814 A | * 10/1980 | Luethi et al. | ............. 134/58 R |
| 4,229,218 A | 10/1980 | Gulla et al. | |
| 4,324,589 A | 4/1982 | Gulla et al. | |
| 4,326,940 A | 4/1982 | Eckles et al. | |
| 4,479,852 A | * 10/1984 | Bindra et al. | ................. 205/81 |
| 4,541,902 A | 9/1985 | Kinoshita et al. | |
| 4,834,842 A | 5/1989 | Langner et al. | |
| 4,886,590 A | 12/1989 | Tittle | |
| 4,895,739 A | 1/1990 | Bladon | |
| 4,917,774 A | 4/1990 | Fisher | |
| 4,917,777 A | 4/1990 | Fisher | |
| 4,948,473 A | 8/1990 | Phillippi | |
| 4,952,286 A | 8/1990 | Bladon et al. | |
| 5,007,990 A | 4/1991 | Bladon | |
| 5,192,403 A | 3/1993 | Chang et al. | |
| 5,196,096 A | 3/1993 | Chang et al. | |
| 5,223,118 A | 6/1993 | Sonnenberg et al. | |
| 5,234,573 A | 8/1993 | Takami | |
| 5,364,510 A | 11/1994 | Carpio | |
| 5,368,715 A | 11/1994 | Hurley et al. | |
| 5,389,215 A | 2/1995 | Horiuchi et al. | |
| 5,391,271 A | 2/1995 | Ludwig | |
| 5,484,626 A | 1/1996 | Storjohann et al. | |
| 5,534,128 A | 7/1996 | Aso et al. | |
| 5,635,043 A | * 6/1997 | Tur yan et al. | ............. 204/412 |
| 6,113,769 A | 9/2000 | Uzoh et al. | |
| 6,235,123 B1 | * 5/2001 | Millar | ........................ 134/26 |
| 6,254,760 B1 | 7/2001 | Shen et al. | |
| 6,280,602 B1 | 8/2001 | Robertson | |
| 6,365,033 B1 | 4/2002 | Graham et al. | |
| 6,471,845 B1 | 10/2002 | Dukovic et al. | |
| 6,551,479 B1 | 4/2003 | Graham et al. | |

* cited by examiner

## AUTOMATED CHEMICAL MANAGEMENT SYSTEM HAVING IMPROVED ANALYSIS UNIT

CROSS-REFERENCE TO RELATED APPLICATIONS

This application is a continuation-in-part of U.S. patent application Ser. No. 09/387,084, filed Aug. 31, 1999, titled "Methods and Apparatus for Controlling and/or Measuring Additive Concentration in an Electroplating Bath" (now issued as U.S. Pat. No. 6,356,033), which is a continuation of PCT/US99/09659, filed May 3, 1999 and published in English under PCT Article 21(2), titled "Methods and Apparatus for Controlling and/or Measuring Additive Concentration in an Electroplating Bath", which claims priority from U.S. Provisional Patent Application Serial No. 60/083,882, filed May 1, 1998, entitled "Closed Loop Electrolyte Composition Monitoring and Control System for Copper Interconnect Applications". The disclosures of these applications are incorporated herein by reference in their entireties.

STATEMENT REGARDING FEDERALLY SPONSORED RESEARCH OR DEVELOPMENT

Not Applicable

BACKGROUND OF THE INVENTION

Electroplating is a complex process involving multiple ingredients in the plating bath. If the plating bath is to provide high-quality electroplating films on the surface of the substrate, the concentration of several of the constituents of the bath should be maintained. As such, the ability to monitor and control the composition of the bath is a key factor in ensuring uniform and reproducible deposit properties. In semiconductor and microelectronic component applications, the electronic and morphological properties of the metal films are of principal importance in determining final device performance and reliability. The stability of later microfabrication processes in the manufacturing sequence frequently depend on repeatable mechanical properties including modulus, ductility, hardness, and surface texture of the electroplating metal. All of these deposit properties are controlled or strongly influenced by the composition of the electroplating bath.

Of particular importance is measurement and control of proprietary organic compounds that serve to modify the deposit properties through adsorption onto and desorption from the cathode surface during plating, thereby affecting the diffusion rate of metal cations to nucleation and growth sites. These compounds are typically delivered as multi-component packages from plating chemistry vendors. One of the functions of the additive packages is to influence the throwing power of the electroplating bath: the relative insensitivity of plating rate to variations in cathodic current density across the wafer or in the vicinity of surface irregularities. The throwing power of the electrolyte has an effect on the cross-wafer uniformity of plated film thickness and the success with which ultrafine trenches and vias (holes) are filled without included seams or voids. Organic additives have also been shown to have substantial effects on mechanical film properties. Detection and quantification of these bath constituents is complicated by the fact that they are effective at very low concentrations in the electrolyte, for example, at several ppm or less.

Plating bath analysis for microelectronic applications is strongly driven by the need to limit variability and maintain device yields through maintenance of optimized process parameters. One method for controlling such ingredients in an electroplating bath is to make regular additions of particular ingredients based upon empirical rules established by experience. However, depletion of particular ingredients is not always constant with time or use. Consequently, the concentration of the ingredients is not actually known and the level in the bath eventually diminishes or increases to a level where it is out of the acceptable concentration range. If the additive content concentration deviates too far from the target value, the quality of the metal deposit suffers and the deposit may be dull in appearance and/or brittle or powdery in structure. Other possible consequences include low throwing power and/or plating folds with bad leveling.

A common method for evaluating the quality of an electroplating bath is disclosed in Tench U.S. Pat. No. 4,132,605 (hereafter the Tench patent). In accordance with the procedures of the Tench patent, the potential of a working electrode 10 is swept through a voltammetric cycle, including a metal plating range and a metal stripping range, for at least two baths of known plating quality and an additional bath whose quality or concentration of brightener is to be evaluated. The integrated or peak current utilized during the metal stripping range is correlated with the quality of the bath of known quality. The integrated or peak current utilized to strip the metal in the bath of unknown quality is compared to the correlation and its quality evaluated. In a preferred embodiment of said patent, the potential of an inert working electrode 10 is swept by a function generator through the voltammetric cycle. An auxiliary electrode 20 immersed in the plating bath is coupled in series with a function generator and a coulometer to measure the charge from the working electrode 10 during the stripping portion of the cycle.

An improvement to the method disclosed in the Tench patent is described by Tench and White, in the *J. Electrochem. Soc.*, "Electrochemical Science and Technology", April, 1985, pp. 831–834(hereafter the Tench publication). In accordance with the Tench publication, contaminant buildup in the copper plating bath affects the copper deposition rate and thus interferes with brightener analysis. The Tench publication teaches a technique that involves sequentially pulsing the electrode between appropriate metal plating, metal stripping, cleaning, and equilibrium potentials whereby the electrode surface is maintained in a clean and reproducible state. This method is in contrast to the continuous sweep cycle utilized in the above-referenced patent, a method be used. Stated otherwise, where the process of the Tench patent involves a continuous voltammetric sweep between about −600 mV and +1,000 mV versus a working electrode and back over a period of about 1 minute, the Tench publication pulses the potential, for example at −250 mV for 2 seconds to plate, +200 mV for a time sufficient to strip, +1,600 mV to clean for several seconds, +425 mV for 5 seconds to equilibrate, all potentials referenced to a saturated Calomel electrode, after which the cycle is repeated until the difference between successive results are within a predetermined value, for example, within 2% of one another.

The procedure of the Tench publication provides some improvement over the procedure of the Tench patent, but during continuous use of an electroplating bath and following successive analysis cycles, contaminants build up on the electrodes and analysis sensitivity is lost. Further, such procedures frequently fail when applied to certain used baths. The inability to accurately measure additive concentrations in such used baths effectively reduces the life time of the bath and increases the cost associated with producing, for example, semiconductor integrated circuits and microelectronic components.

BRIEF SUMMARY OF THE INVENTION

A method and apparatus for measuring a target constituent of an electroplating solution using an electroanalytical technique is set forth. In accordance with the method, a pair of electrodes are employed to execute the electroanalytical technique. Gasses that are trapped or generated at the surface of one or both of the electrodes of the pair are reduced and/or removed by directing a flow of the electroplating solution toward the electrode surface. This flow of solution against the electrode surface acts to automatically flush the generated gasses (typically in the form of small bubbles) from the electrode surface and generally eliminates the need for manual purging by an operator. Elimination of these gasses reduces or eliminates variability in the open circuit potential, and concomitant noise that would otherwise occur in the electroanalytical measurements.

DETAILED DESCRIPTION OF ONE OR MORE EMBODIMENTS OF THE INVENTION

In order to comprehend the context of the present invention, an understanding of the various techniques suitable for analyzing an electroplating bath is helpful. To this end, a description of certain electroplating bath analysis techniques are set forth.

A major category of analysis suitable for monitoring an electroplating bath is electroanalysis. Electroanalytical methods use electrically conductive probes, called electrodes, to make electrical contact with the electroplating solution. The electrodes are used in conjunction with electronic devices to which they are attached to provide electrical energy to the solution and measure a corresponding electrical parameter of the electroplating solution. The measured parameter, in turn, is indicative of the type and/or quantity of additives in the electroplating solution.

Faradaic electroanalysis is attractive as an investigative analytical method principally because what is studied is the electrochemical activity of the bath sample under applied electrical stimulus; the measured responses are related in a fundamental way to the properties which influence the quality of the metal deposition process itself. Electroanalysis further offers the opportunity to study the mechanisms and kinetics of the plating process, and the influences the various bath components exert on plating rate suppression and acceleration.

Generally stated, electroanalytical methods are divided into categories according to the electrical parameters that are measured. The major electroanalytical methods include potentiometry, amperometry, conductometry, voltammetry (and polarography), and coulometry. The names of the methods reflect the measured electrical property or its units. Potentiometry measures electric potential (or voltage) while maintaining a constant electric current between the electrodes. Amperometry monitors electric current (amperes). Conductometry measures conductance (the ability of a solution to carry an electric current). Voltammetry is a technique in which the potential is varied in a regular manner while the current is monitored. Coulometry is a method that monitors the quantity of electrical charge (coulombs) that is consumed during an electrochemical reaction involving the analyte. Voltammetry (or amperometry) involves the investigation of the current which develops in an electrochemical cell as a consequence of applied potential between a working and auxiliary electrode pair, with the potential measured against a suitable reference electrode. As will become apparent, the electroanalytical cell disclosed herein is suitable for use in connection with all of these electroanalytical methods.

Figure 1:
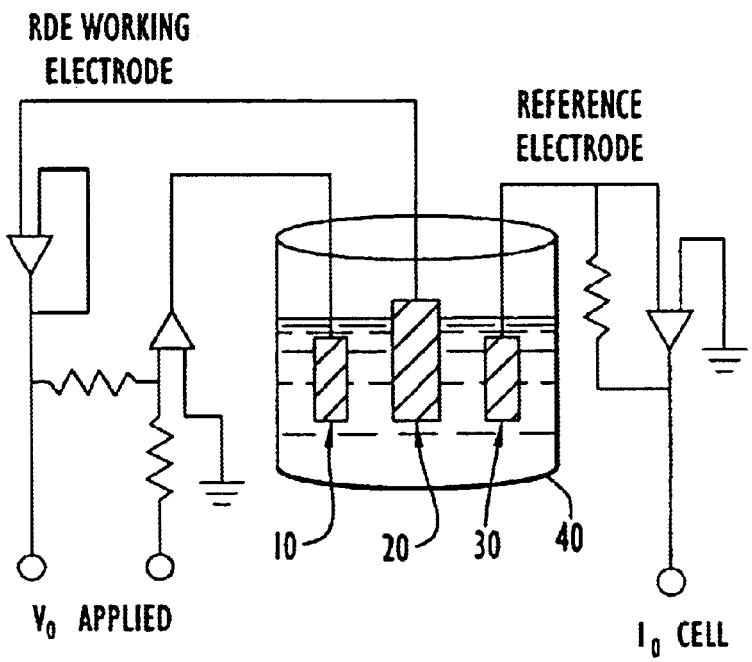
FIG. 1 is a schematic diagram of an exemplary analytical cell used to measure one or more constituents of an electroplating bath.

FIG. 1 shows the schematic wiring diagram for a basic electroanalytical cell. Three electrodes: a working electrode 10, auxiliary electrode 20, and a reference electrode 30, are immersed in an electroanalytical cell, 40. The reference electrode 30 may, for example, be a Ag/AgCl double junction or Saturated Calomel Electrode (SCE). The working electrode 10, for example, may be one of several types, including the dropping mercury electrode (DME), hanging mercury drop electrode (HMDE), mercury thin film electrodes (MTFE), or an inert electrode which may be either stationary or of a rotating electrode (RDE, RRDE, RCE) configuration. While the mercury-based electrodes offer the advantage of a surface that can be periodically 'renewed' to offer immunity to drift in electrochemical responses associated with changes in surface conditions (e.g., deposit build-up or smutting), inert RDE-type working electrodes with Pt, Pd, Ir, or Rh surfaces are most often employed in systems dedicated to plating bath analysis for convenience of system set-up, maintenance, and waste handling. FIG. 1 illustrates use of an RDE-type electrode in which relative motion between the working electrode 10 and the bath is established by a motor (see FIG. 3) that rotates the working electrode 10. Electrical contact to the working electrode 10 is made by, for example, slip brushes, or a mercury contact. Voltammetric cycles can be specified to provide in-situ cleaning of the RDE surface, and analytical methods are known which minimize the influence of slight changes in the electrode surface state over time. Potentiometry is conducted in identical apparatus, with evaluation of the voltage between the working and auxiliary electrodes required to maintain a forced current.

A computer is used to control an electronic potentiostat that controls the energy input between the working electrode 10 and the reference electrode 30. For laboratory testing of the method, instrumentation such as a Pine Instruments potentiostat under IBM computer control may be used. Using a suitable program, the energy input sequences may be applied to the working electrode 10. The output of the device can also be plotted on an X-Y recorder to graphically display the changes in energy output versus time for each step. The terms "energy input" and "energy output" in the following description of the methods will refer to control of the potential (energy input) while monitoring current density (energy output), or control of current density (energy input) while monitoring potential (energy output).

Figure 2:
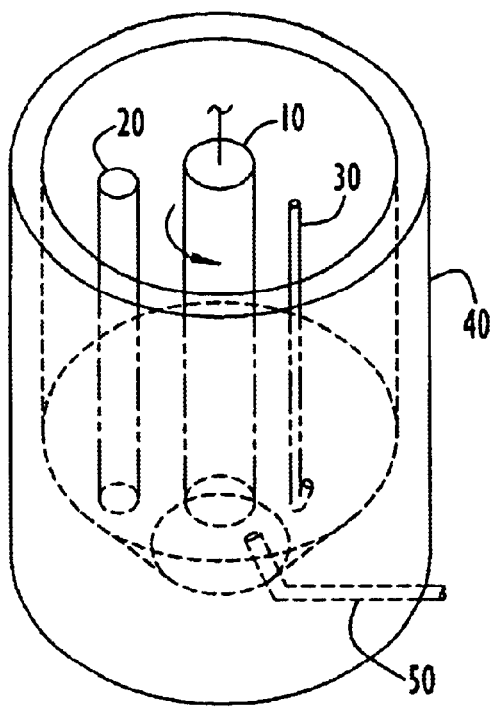
FIG. 2 is a perspective view of one embodiment of an analytical cell constructed in accordance with the teachings of the present invention.
Figure 3:
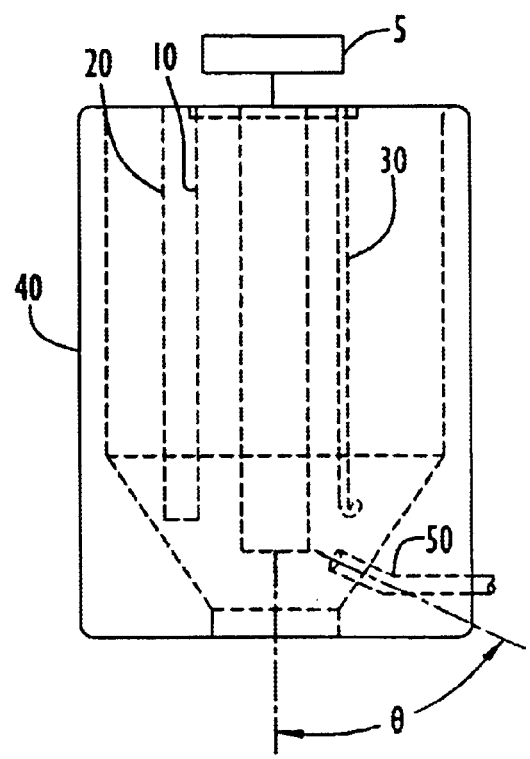
FIG. 3 is a side elevation view of the analytical cell illustrated in FIG. 2.
Figure 4:
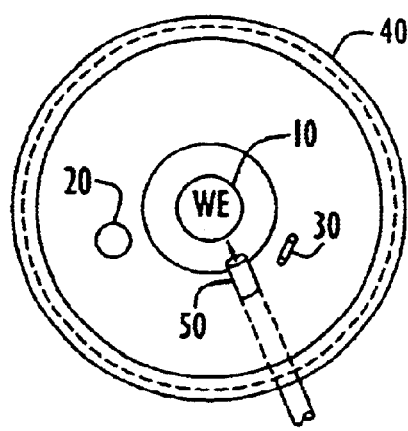
FIG. 4 is a top plan view of the analytical cell illustrated in FIG. 2.

FIGS. 2, 3, and 4 illustrate one embodiment of an electroanalytical cell 40 constructed in accordance with the teachings of the present invention. As shown, the electroanalytical cell 40 includes a working electrode 10, an auxiliary electrode 20, and a reference electrode 30 that are positioned so that they are at least partially submerged in the electroplating solution. In the disclosed embodiment, reference electrode 30 is of the J-tube, pool type, with working electrode 10 preferably being movable relative to the electroplating solution. For example, working electrode 10 may be configured as a rotating disc electrode (RDE). Electroanalytical cell 40 may also include an insulating material or insulating jacket at its exterior to control the temperature at which electroanalytical measurements are made. Control of the temperature increases the overall accuracy of a given measurement and, further, increases sample-to-sample measurement accuracy.

Electrochemical analyses that are performed using a rotating disc electrode, such as electrode 10, can be problematic. One problem that frequently arises is the formation of gases at the exterior surfaces of the electrode 10. These gases may accumulate to form bubbles at the electrode surface that interfere with the electroanalytical processes that are implemented in the electroanalytical cell 40, or that change the effective surface area of the working electrode, 10. This gaseous accumulation may originate from a number of different sources. For example, bubbles may be entrapped as the electroanalytical cell 40 is filled with the bath sample that is to be analyzed. Further, gases may be electrochemically formed during the analysis through a reduction ($H_2$ gas) or oxidation ($O_2$) reaction. Once such gases form at the surface of the electrode, physical intervention to effect removal of the gases is ordinarily required. Removal is typically performed by the operator of the system by wiping the bubbles off of the electrode. However, manual manipulation of the electrode introduces its own set of problems. For example, the operator may inadvertently deposit contaminants or the like onto the surface of the electrode. Further, the operator may introduce a further amount of entrapped gases into the system during the manipulation.

In order to flush such gases from the surface of the working electrode 10, the illustrated embodiment of the electroanalytical cell 40 includes at least one nozzle 50 that is oriented to direct a flow of solution toward the surface of the electrode 10. This flow may be generated by a recirculating pump (not illustrated) that recirculates the sample of the electroplating solution under analysis through the electroanalytical cell 40. The flow from nozzle 50, in turn, shears gases that have formed at the surface of electrode 10. Bubbles and like gaseous formations are thus automatically flushed from the electrode surface without the need for user intervention and the appertaining manual manipulation of the electrode 10. Elimination of the gases reduces or eliminates variability in the open circuit potential, and the concomitant noise in the electrical response of the system that would otherwise occur if the gases were not removed.

In the illustrated embodiment, solution is directed by nozzle 50 at an acute angle "theta" relative to the longitudinal axis of the electrode 10 (see FIG. 3). This angular configuration of the nozzle 50 enhances the shearing action of the flow with respect to the electrode surface and makes the flow more effective in removing the gases. As an example, this angle may be greater than or about 45 degrees.

Figure 5:
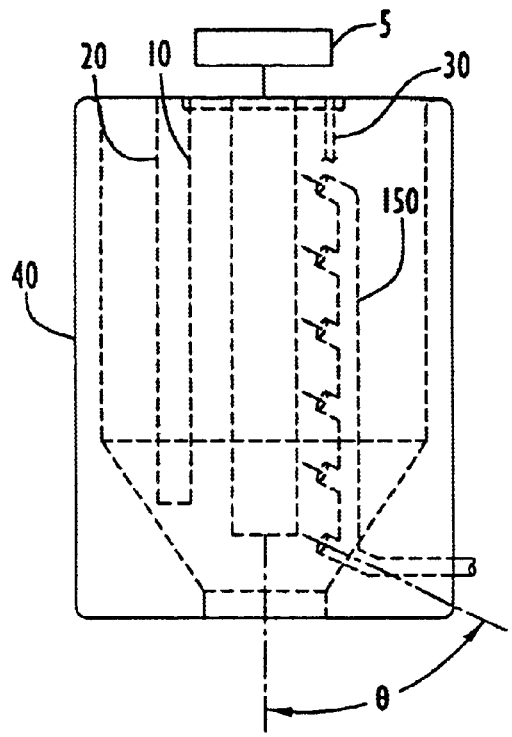
FIG. 5 is a side elevation view of a further embodiment of an analytical cell constructed in accordance with the teachings of the present invention.

FIG. 5 illustrates a further embodiment of an electroanalytical cell 40 constructed in accordance with the teachings of the present invention. As shown, this embodiment includes a nozzle arrangement that comprises a nozzle manifold 150 having a plurality of nozzles extending therefrom. The plurality of nozzles extend from the nozzle manifold 150 and are spaced apart along the longitudinal axis of the electrode 10. In order to enhance the shearing action of the electroplating solution flow, each of the nozzles may be arranged at an angle "theta" relative to the longitudinal axis of the electrode 10. This embodiment is particularly effective when the electrode 10 is a stationary electrode, when large amounts of gas evolve at the surface of the electrode, or when gas must be flushed from the surface using a low flow rate of the electroplating solution.

Figure 6:
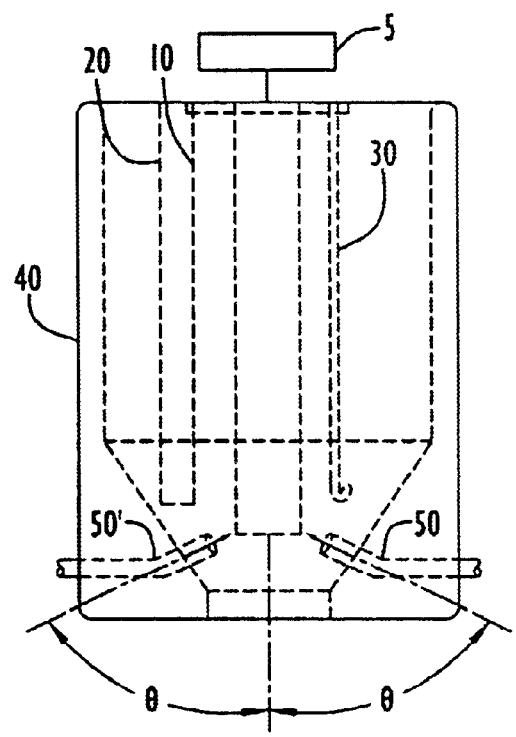
FIG. 6 is a side elevation view of a still further embodiment of an analytical cell constructed in accordance with the teachings of the present invention.
Figure 7A:
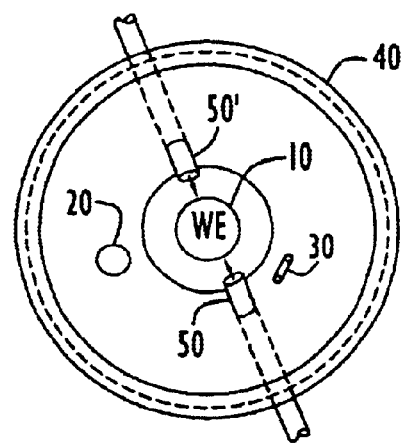
FIG. 7A is a top plan view of the analytical cell illustrated in FIG. 6.

FIGS. 6 and 7A illustrate a further alternate embodiment of the electroanalytical cell configuration, including a plurality of nozzles, including nozzles 50, 50', for directing electroplating solution against the electrode 10. In this embodiment, the nozzles 50, 50' are arranged in generally mirror-image relationship with respect to the electrode 10, and are thus configured to direct electroplating solution against diametrically opposed surfaces of the electrode 10. In order to enhance the flushing action of the solution, each of the nozzles 50, 50' may be arranged to direct solution at an acute angle "theta" relative the longitudinal axis of the electrode 10.

Figure 7B:
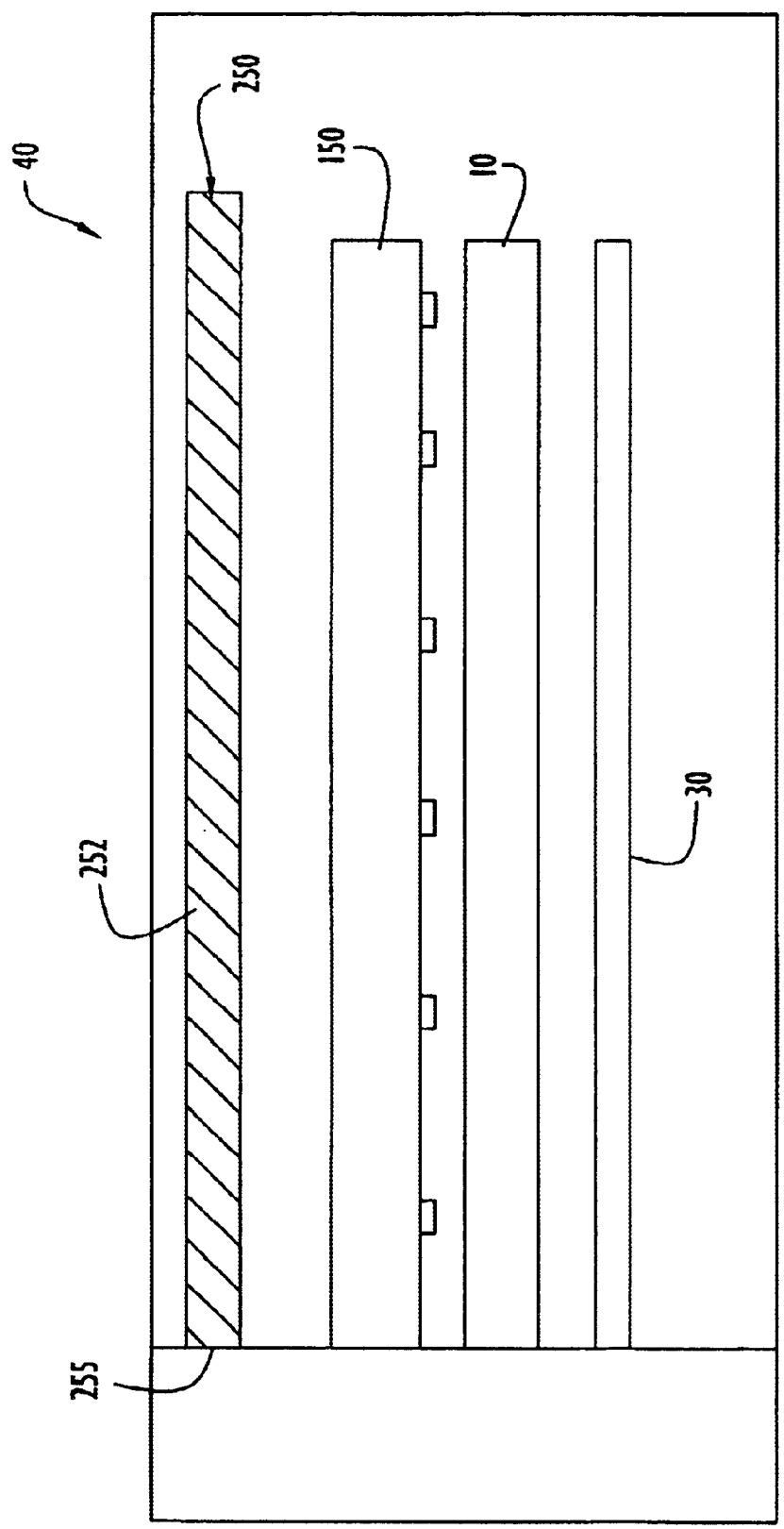
FIG. 7B is a side elevation view of a still further embodiment of an analytical cell constructed in accordance with the teachings of the present invention.

FIG. 7B illustrates an embodiment of electroanalytical cell 40 in which one or more of the various elements making up the cell are oriented horizontally. In the illustrated embodiment, the longitudinal axis of the electrode 20 is oriented horizontally, as are the other elements of the cell 40. The cell 40 may include a horizontal nozzle arrangement, including a nozzle manifold 150, such as the one set forth in FIG. 5 above. Alternatively, it may include a single nozzle arrangement. The nozzle arrangement may be positioned about any peripheral portion of electrode 20. However, it may be advantageous to place the nozzle arrangement vertically above electrode 20 so that the tendency of the bubbles to rise within the solution enhances their removal from the electrode. Once removed in this manner, the bubbles may be extracted from the cell 40 by a vent assembly 250 or the like. In the illustrated embodiment, the vent assembly 250 is in the form of one or more slanted walls 252 that terminates at a vent opening in 255.

One or more of the foregoing electroanalytical cells, as well as modified versions thereof, may be used in conjunction with an automated dosing system. As the microelectronics fabrication industry moves toward widespread use of electroplating, particularly of microstructures, there is an increased need for highly accurate dosing systems that replenish the various components of the electroplating bath. To this end, dosing systems have been developed for use with electroplating tools that are used at microelectronic fabrication facilities. Most known systems, however, execute the dosing function using open-loop, predetermined models that replenish the electroplating bath constituents based on empirically determined data. Such systems may be suitable for certain electroplating processes, but become less viable as new device requirements impose more rigorous standards on the make-up of the electroplating bath.

Figure 8:
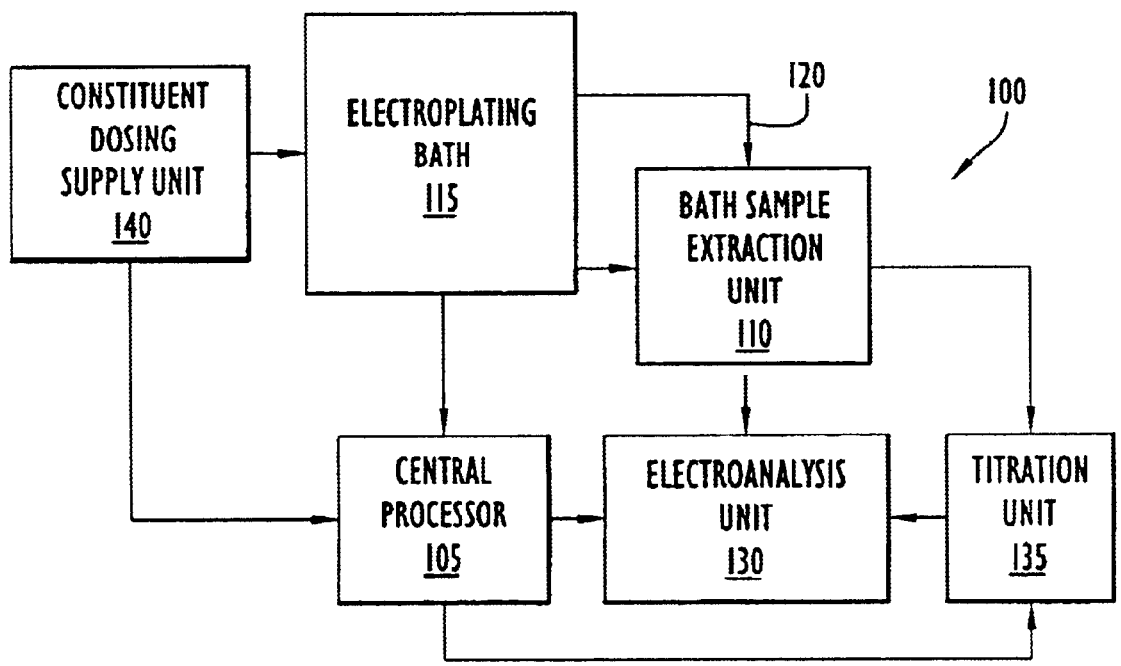
FIG. 8 is a schematic block diagram of on e embodiment of a dosing system that uses an analytical cell to execute an electroanalytical measurement technique as part of a feedback process to replenish an electroplating bath with a target constituent.

More accurate control of the plating bath constituents may be obtained using a dosing system that employs measurement feedback to ascertain the proper quantity of a bath constituent that is to be added. An exemplary feedback dosing system that may include an electroanalytical cell 40 is illustrated in FIG. 8. As shown, the dosing system, shown generally at 100, includes a central processor 105 that is used to control the operations necessary to perform the following functions: 1) extract a sample of the electroplating bath that is to be analyzed; 2) execute an electroanalytical technique on the electroplating bath sample; 3) calculate the amount of the electroplating bath constituent present in the sample based on the results of the electroanalytical technique; and 4) use the resulting calculation to automatically control the supply of an amount of the constituent to replenish the electroplating bath, raising the constituent concentration to a predetermined level. To increase the accuracy of measurements taken in the electroanalytical cell 40, the central processor 105 may be connected to control the recirculation pump. For example, central processor 105 may be used to control the flow rate through the recirculation pump. as well as schedule the time during which a given flow rate is employed. This arrangement provides for a high degree of electroanalytical measurement programmability.

In order to execute the remaining functions noted above, the central processor 105 is connected to interact with and exchange information with a number of further units and systems. A bath sample extraction unit 110 is connected for control by the central processor 105. The bath sample extraction unit 110 is connected to receive electroplating solution along line 120 from the principal electroplating bath 115 in response to control signals/commands received from the central processor 105 along a suitable communication link (not illustrated). In response to such control signals/commands, the bath sample extraction unit 110 provides the bath sample to either an electroanalytical cell 40 of electroanalysis unit 130 or to an optional titration system 135.

Both the electroanalysis unit 130 and the optional titration system 135 are under the control of the central processor 105. The central processor 105 coordinates the activities of the electroanalysis unit 130 and titration system 135 to execute the desired electroanalytical technique. The electroanalytical technique can be any of the known techniques, or can be one or more of the inventive techniques such as those disclosed in U.S. Ser. No. 09/387,084, entitled "Methods and Apparatus for Controlling and/or Measuring Additive Concentration in an Electroplating Bath", filed Aug. 31, 1999.

The central processor 105 that acquires the requisite data based on the electroanalytical technique to directly calculate or otherwise determine in a relative manner the concentration of the plating bath constituent. Based on this calculation/determination, the central processor 105 directs one or more constituent dosing supply units 140 to provide the necessary amount of the constituent (or amount of solution containing the constituent) to the electroplating bath 115, thus completing the feedback control process.

It will be recognized that the electroanalytical apparatus and techniques described above can be implemented in a manual, semi-automatic, or completely automatic manner. Dosing system 100 is provided as an illustrative, yet novel manner in which to implement one or more known and/or inventive electroanalytical techniques described above.

Numerous modifications may be made to the foregoing system without departing from the basic teachings thereof. Although the present invention has been described in substantial detail with reference to one or more specific embodiments, those of skill in the art to the will recognize that changes may be made thereto without departing from the scope and spirit of the invention as set forth in the appended claims.

What is claimed is:

1. An electroanalytical cell comprising:
   an electrode disposed for contact with an electrolyte that is to be analyzed; and
   a plurality of nozzles proximate the electrode and oriented to direct a flow of solution toward the electrode for purging gases therefrom.

2. The electroanalytical cell of claim 1 wherein the electrode is selected from the group consisting of a rotating disk electrode, a rotating ring disk electrode, and a rotating cylinder electrode.

3. The electroanalytical cell of claim 1 wherein the plurality of nozzles are oriented to direct the flow of solution at an angle with respect to a longitudinal axis of the electrode.

4. The electroanalytical cell of claim 1 and further comprising a manifold connected to and supporting the plurality of nozzles.

5. The electroanalytical cell of claim 4 wherein the plurality of nozzles are disposed generally parallel to a longitudinal axis of the electrode.

6. The electroanalytical cell of claim 5 wherein the plurality of nozzles are oriented to direct the flow of solution at an angle with respect to the longitudinal axis of the first electrode.

7. A method for measuring a target constituent of an electroplating solution, the method comprising the steps of:
   placing an amount of the electroplating solution into an electroanalytical cell comprising at least two electrodes;
   purging gases formed at the surface of at least one of the two electrodes by directing a flow of solution through a plurality of nozzles toward the surface;
   providing an energy input to the at least two electrodes;
   taking an electroanalytical measurement of the energy output response of the electroplating solution to the energy input that was provided to the at least two electrodes; and
   using the electroanalytical measurement to determine an amount of the target constituent in the electroplating solution.

8. A method as claimed in claim 7 wherein the step of purging further comprises moving said at least one electrode relative to said electroplating solution while directing flow of said solution thereagainst.

9. A method as claimed in claim 7 wherein the flow of solution used in the step of purging is directed at an angle relative to a longitudinal axis of said at least one electrode.

10. A method as claimed in claim 7 wherein at least the flow of the plurality of nozzles are spaced apart from each other along a longitudinal axis of said at least one electrode.

11. A method as claimed in claim 10 wherein the step of purging further comprises directing the flow of solution at an angle, relative to said longitudinal axis, through said plurality of nozzles.

12. A method as claimed in claim 10 wherein the step of purging further comprises directing the flow of solution against diametrically opposed surfaces of said at least one electrode.

13. A method as claimed in claim 12 wherein the step of purging further comprises directing the flow of solution at an angle relative to a longitudinal axis of said at least one electrode.

14. An apparatus for maintaining a concentration level of a target constituent of an electroplating bath comprising:
    a bath sample extraction unit configured to connect to an electroplating tool in order to automatically remove a sample of the electroplating bath from an electroplating tool;
    an electroanalysis unit configured to receive the bath sample obtained by the bath sample extraction unit;
    an electroanalytical cell forming part of the electroanalysis unit, the electroanalytical cell including:
        a first electrode positioned for contact with the bath sample,
        a second electrode positioned for contact with the bath sample, and
        at least one nozzle proximate the first electrode that is disposed to direct a flow of solution bath sample toward a surface of the first electrode;
    a constituent dosing supply unit configured to provide an amount of the target constituent to the electroplating bath of the electroplating tool;
    a programmable control unit connected to communicate with:
        a) the bath sample extraction unit for control of the extraction of the bath sample from the electroplating bath of the electroplating tool and supply of the bath sample to the electroanalysis unit,
        b) the electroanalysis unit to execute an electroanalytical technique to determine an amount of the target constituent in the bath sample, and
        c) the constituent dosing supply unit to provide an amount of the target constituent to the electroplating bath of the electroplating tool based on the amount of the target constituent measured in the bath sample through the use of the electroanalytical technique.

15. The apparatus of claim 14 wherein said at least one nozzle is configured to direct the flow of solution sample against said first electrode at an angle relative to a longitudinal axis of said first electrode.

16. The apparatus of claim 14 wherein said first electrode comprises a rotating disk electrode, a rotating ring disk electrode, or a rotating cylinder electrode.

17. The apparatus of claim 14 wherein said at least one nozzle comprises a plurality of nozzles that direct said solution against said first electrode.

18. The apparatus of claim 17 and further comprising a nozzle manifold supporting the plurality of nozzles, the plurality of nozzles being spaced along a longitudinal axis of said first electrode.

19. The apparatus of claim 17 wherein each of said plurality of nozzles is oriented to direct the flow of solution against said first electrode at an angle relative to a longitudinal axis of said first electrode.

20. The apparatus of claim 17 wherein said plurality of nozzles comprises a pair of nozzles positioned to direct the sample bath against diametrically opposed surfaces of said first electrode.

21. A method for measuring a target constituent of an electroplating bath in an electroplating tool, comprising:
    automatically extracting a sample of the electroplating bath from the electroplating tool via a bath sample extraction unit;
    introducing the sample in an electrolytic cell including an electrode positioned within the electrolytic cell to contact the sample;
    performing an electroanalytical technique within the electrolytic cell to determine an amount of the target constituent within the bath sample;
    directing a flow of solution toward the electrode via at least one nozzle to remove gases formed at surface portions of the electrode; and
    automatically providing an amount of the target constituent, via a constituent dosing supply unit, to the electroplating tool based upon the determined amount of the target constituent within the bath sample.

22. The method of claim 21 wherein the directing step includes directing solution toward the electrode at an angle relative to a longitudinal axis of the electrode.

23. The method of claim 21 wherein the at least one nozzle comprises a plurality of nozzles.

24. The method of claim 23 wherein the plurality of nozzles are spaced along a longitudinal axis of the electrode.

25. The method of claim 21 wherein the directing step includes directing the solution against diametrically opposed surfaces of the electrode.

26. The method of claim 21, wherein the electrode is selected from the group consisting of a rotating disk electrode, a rotating ring disk electrode, and a rotating cylinder electrode.

* * * * *